United States Patent

Kaplan et al.

[11] 4,005,105
[45] Jan. 25, 1977

[54] SUBSTITUTED 10-ETHYNYLDIBENZO[b,f]THIEPINS AND DIBENZ[b,f]OXEPINS

[75] Inventors: Jean-Pierre Kaplan, Le Plessis Robinson, France; Emilio Kyburz, Reinach, Switzerland

[73] Assignee: Hoffmann-La Roche Inc., Nutley, N.J.

[22] Filed: Sept. 15, 1975

[21] Appl. No.: 613,680

Related U.S. Application Data

[60] Division of Ser. No. 500,770, Aug. 26, 1974, Pat. No. 3,928,383, which is a continuation-in-part of Ser. No. 380,653, July 12, 1973, abandoned.

[30] Foreign Application Priority Data

June 8, 1973 Switzerland ............... 8354/73
May 10, 1974 Switzerland ............... 6421/74

[52] U.S. Cl. ..................... 260/327 B; 260/333
[51] Int. Cl.² ............................ C07D 337/14
[58] Field of Search ................ 260/327 B, 333

[56] References Cited

UNITED STATES PATENTS

| 3,100,207 | 8/1963 | Zirkle | 260/268 |
| 3,641,056 | 2/1972 | Schindler et al. | 260/333 |
| 3,787,444 | 1/1974 | Gosteli | 260/327 B |

FOREIGN PATENTS OR APPLICATIONS

| 7,588 | 1964 | Netherlands |
| 6,494 | 1964 | South Africa |
| 443,344 | 1964 | Switzerland |

OTHER PUBLICATIONS

Protiva, Monatsheft fur Chemie, Band 96(1), 1965, pp. 182–207.

*Primary Examiner*—Cecilia M.S. Jaisle
*Attorney, Agent, or Firm*—Samuel L. Welt; Bernard S. Leon; William G. Isgro

[57] ABSTRACT

Compounds of the formulas

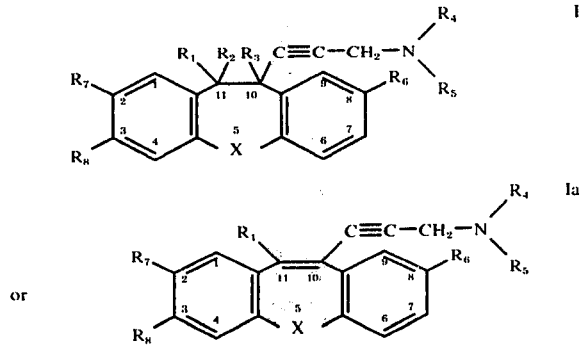

wherein $R_1$, $R_2$, $R_3$, $R_4$, $R_5$, $R_6$, $R_7$, $R_8$ and X are as hereinafter set forth, are described. The compounds of formulas I and Ia are useful as neuroleptic agents.

2 Claims, No Drawings

SUBSTITUTED 10-ETHYNYLDIBENZO[B,F]THIEPINS AND DIBENZ[B,F]OXEPINS

CROSS-REFERENCE TO RELATED APPLICATIONS

This is a division, of application Ser. No. 500,770 filed Aug. 26, 1974, now U.S. Pat. No. 3,928,383, issued Dec. 23, 1975, which in turn is a continuation-in-part of Ser. No. 380,653, filed July 12, 1973, now abandoned.

BRIEF SUMMARY OF THE INVENTION

The invention relates to compounds of the formulas

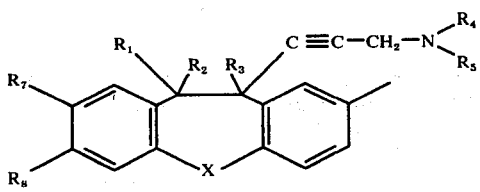

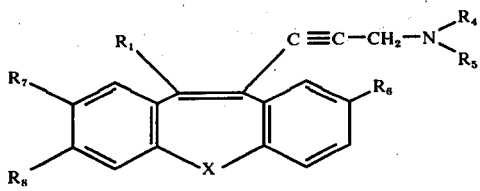

wherein X is oxygen or sulfur; $R_1$ and $R_2$, independently, are hydrogen or lower alkyl; $R_3$ is hydrogen; $R_4$ and $R_5$, independently, are hydrogen, lower alkyl, hydroxy-lower alkyl, alkanoyloxy-lower alkyl or, when taken together, are a saturated 5-or 6-membered heterocyclic ring, which may contain an oxygen, a sulfur or an additional nitrogen atom, and which may be substituted by lower alkyl, hydroxy-lower alkyl or alkanoyloxy-lower alkyl; $R_6$ is lower alkyl, lower alkylsulfonyl, hydroxy, lower alkoxy, lower alkythio, di-(lower alkyl)-sulfamoyl, halogen, trifluoromethyl, nitro, amino or di-(lower alkyl)amino; and $R_7$ and $R_8$; independently, are hydrogen, lower alkyl, lower alkoxy, lower alkyl-sulfonyl, hydroxy, lower alkylthio, di-(lower alkyl)-sulfamoyl, halogen, trifluoromethyl, nitro, amino or di-(lower alkyl)-amino,
and the corresponding N-oxides and the pharmaceutically acceptable acid addition salts thereof.

DETAILED DESCRIPTION OF THE INVENTION

The invention relates to compounds of the formulas

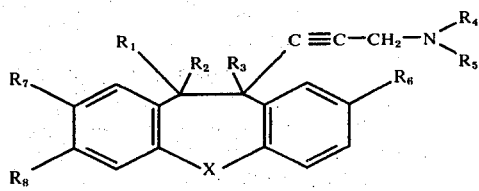

and

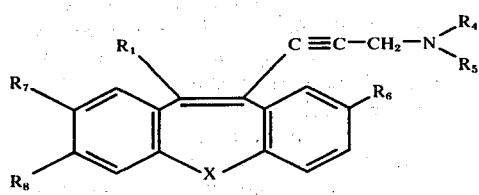

wherein X is oxygen or sulfur; $R_1$ and $R_2$, independently, are hydrogen or lower alkyl; $R_3$ is hydrogen; $R_4$ and $R_5$, independently, are hydrogen, lower alkyl, hydroxy-lower alkyl, alkanoyloxy-lower lower alkyl or, when taken together, are a saturated 5- or 6- membered heterocyclic ring, which may contain an oxygen, a sulfur or an additional nitrogen atom, and which may be substituted by lower alkyl, hydroxy-lower alkyl or alkanoyloxy-lower alkyl; $R_6$ is lower alkyl, lower alkyl-sulfonyl, hydroxy, lower alkoxy, lower alkylthio, di-(lower alkyl)-sulfamoyl, halogen, trifluoromethyl, nitro, amino or di-(lower alkyl)-amino; and $R_7$ and $R_8$,

I

Ia and the corresponding N-oxides and the pharmaceutically acceptable acid addition salts thereof.

As used herein, the term "lower alkyl" denotes a straight chain or branched chain hydrocarbon of 1–7 carbon atoms, for example, methyl, ethyl, propyl, butyl, and the like. The term "lower alkoxy" denotes a lower alkyl ether group in which the lower alkyl moiety is as defined above, for example, methoxy, ethoxy, propoxy, butoxy, and the like. The term "lower alkylthio" denotes a lower alkylthio ether group in which the lower alkyl moiety is as defined above, for example, methylthio, ethylthio, propylthio, butylthio, and the like. The term alkanoyloxy denotes a straight or branched chain lower alkanoyloxy group of 2–18 carbon atoms, preferably of 2–10 carbon atoms, for example, acetoxy, pivaloyloxy, pentanoyloxy, hexanoyloxy, heptanoyloxy, octanoyloxy, nonanoyloxy, decanoyloxy, tetradecanoyloxy, hexadecanoyloxy, octadecanoyloxy, and the like. The 5- or 6-membered heterocyclic rings which may contain two nitrogen atoms, or one nitrogen atom, or one nitrogen atom and an oxygen or sulfur atom are exemplified by pyrrolidino, piperazino, piperidino, morpholino, thiomorpholino, methylpiperidino, and the like. The lower alkyl, hydroxy-lower alkyl, or alkanoyloxy-lower alkyl which may be substituted on the heterocyclic moiety is preferably connected to the second nitrogen of the piperazine moiety; exemplary of such are N-methylpiperazino, N-hydroxyethylpiperazino, N-hydroxypropylpiperazino, N-heptanoyloxypropylpiperazino. All the halogens are included, i.e., fluoro, chloro, bromo and iodo. Chloro is preferred.

It has been discovered that the compounds of formulas I and Ia of the invention, their N-oxides and pharmaceutically acceptable salts thereof, demonstrate strong neuroleptic activity. They can, therefore, be utilized for the treatment of, for example, acute or chronic schizophrenia, as well as tranquilizers. Advantageously, the compounds of the invention demonstrate no or only very weak cataleptic side effects, so that no or only insignificant motor disturbances are observed. The compounds of formula Ia are preferred. Preferred compounds of formulas I and Ia of the invention are those wherein $R_1$ is hydrogen.

A preferred subgenus also comprises the compounds of formulas I and Ia wherein X is sulfur. Yet another preferred group of the compounds of the invention are those of formulas I and Ia wherein $R_4$ and $R_5$ are lower alkyl, especially methyl.

Still another preferred subgenus comprises the compounds of formulas I and Ia of the invention, wherein $R_6$ is methylthio or chloro and $R_7$ and $R_8$ are hydrogen. Yet again, those derivatives wherein $R_6$ is chloro, $R_7$ is hydrogen and $R_8$ is methoxy are also preferred. An especially preferred group of the compounds of formula Ia of the invention comprises those wherein $R_1$ is hydrogen, $R_4$ is hydrogen or lower alkyl, $R_5$ is lower alkyl, hydroxy-(lower alkyl) or alkanoyloxy-(lower alkyl), or $R_4$ and $R_5$, taken together with the nitrogen atom to which they are attached are a saturated 5-membered or 6-membered heterocyclic ring which may contain oxygen or an additional nitrogen and which may be substituted by hydroxy-(lower alkyl) or alkanoyloxy-(lower alkyl), $R_6$ is halo or lower alkyl, lower alkoxy, lower alkylthio, lower alkylsulfonyl, di-(lower alkyl)-sulfamoyl, trifluoromethyl, nitro, amino or di-(lower alkyl)-amino, and one of $R_7$ and $R_8$ is hydrogen and the other is halo, lower alkyl or lower alkoxy. Preferred within this last-mentioned group of compounds are those wherein $R_1$ is hydrogen, $R_4$ is hydrogen, methyl or ethyl, $R_5$ is methyl, ethyl, hydroxyethyl or acetoxyethyl or $R_4$ and $R_5$, taken together with the nitrogen atom to which they are attached are piperidino, pyrrolidino, morpholino, N-hydroxyethylpiperazino or N-acetoxyethylpiperazino, $R_6$ is chloro, methyl, methoxy, methylthio, methylsulfonyl, dimethylsulfamoyl, trifluoromethyl, nitro, amino or dimethylamino, $R_7$ is hydrogen, chloro or methyl and $R_8$ is hydrogen, methyl or methoxy. Particularly preferred compounds of the invention are N,N-dimethyl-3-[8-(methylthio)-dibenzo[b,f]thiepin-10-yl]-2-propynylamine, N,N-dimethyl-3-(8-chlorodibenzo[b,f]thiepin-10-yl)-2-propynylamine and N,N-dimethyl-3-(8-chlorodibenzo[b,f]thiepin-10-yl)-2-propynylamine and N,N-dimethyl-3-(8-chloro-3-methoxy-dibenzo[b,f]-thiepin-10-yl)-2-propynylamine, or the pharmaceutically acceptable addition salts thereof.

The tricyclic compounds of formulas I and Ia, as well as their N-oxides and pharmaceutically acceptable salts thereof, can be prepared through processes as hereinafter described:

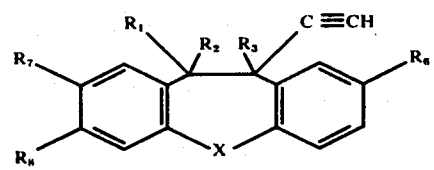

II and

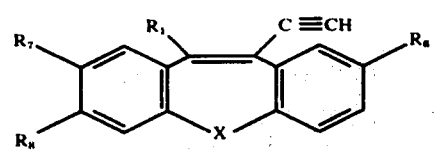

IIa wherein $R_1$, $R_2$, $R_3$, $R_6$, $R_7$, $R_8$ and X are as hereinbefore described, except that a hydroxy group can also be protected, respectively, is reacted with formaldehyde and a compound of the formula

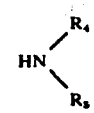

III wherein $R_4$ and $R_5$ are as hereinbefore described, or b. A compound of the formula

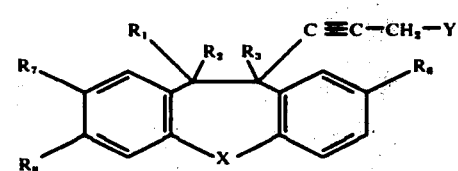

IV and

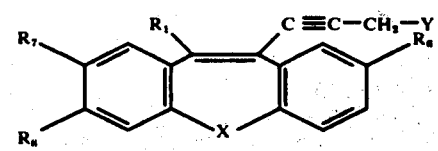

IVa wherein $R_1$, $R_2$, $R_3$, $R_6$, $R_7$, $R_8$ and X are as hereinbefore described, and Y is a leaving group, except that a hydroxy group can also be protected, respectively, is reacted with a compound of the formula

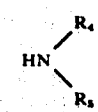

III wherein $R_4$ and $R_5$ are as hereinbefore described, or c. For the preparation of a compound of formula Ia, a compound of the formula

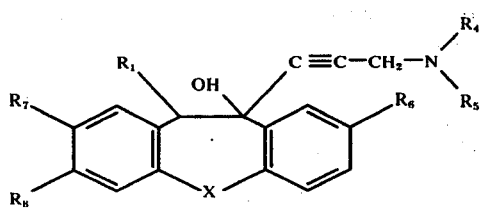

wherein $R_1$, $R_4$, $R_5$, $R_6$, $R_7$, $R_8$ and X are as hereinbefore described, except that a hydroxy group can also be protected, is dehydrated, or d. For the preparation of a compound of formula I or Ia, wherein $R_4$ is hydrogen or lower alkyl and $R_5$ is lower alkyl, a compound of the formula

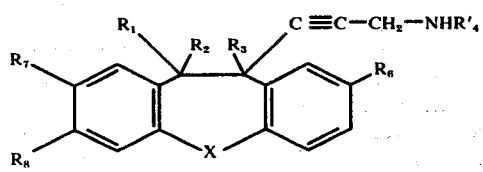

and

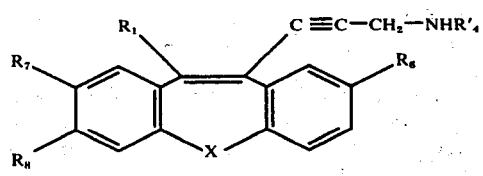

wherein $R_1$, $R_2$, $R_3$, $R_6$, $R_7$, $R_8$ and X are as hereinbefore described, and $R'_4$ is hydrogen or lower alkyl, except that a hydroxy group can also be protected, respectively, is alkylated, or e. For the preparation of an N-oxide of a compound of formula I or Ia wherein $R_4$ and $R_5$ is other than hydrogen, a compound of the formula

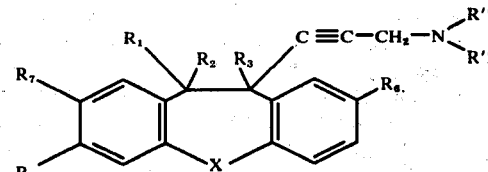

and

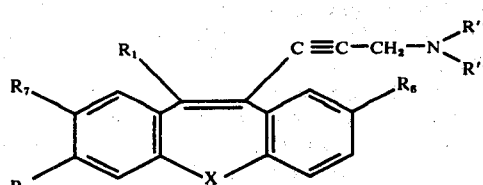

wherein $R_1$, $R_2$, $R_3$, $R_6$, $R_7$, $R_8$ and X are as hereinbefore described; $R''_4$ and $R''_5$ are lower alkyl, hydroxy-(lower alkyl)- or alkanoyloxy-(lower alkyl), or $R''_4$ and $R''_5$, taken together with the nitrogen atom, are a saturated 5-membered or 6-membered heterocyclic ring which may contain oxygen, sulfur or an additional nitrogen and which may be substituted by lower alkyl, hydroxy-(lower alkyl)-, or alkanoyloxy-(lower alkyl)-, respectively, is oxidized; or f. For the preparation of a compound of formula I or Ia wherein $R_4$ is hydrogen and $R_5$ is alkanoyloxy-(lower alkyl), a compound of the formula

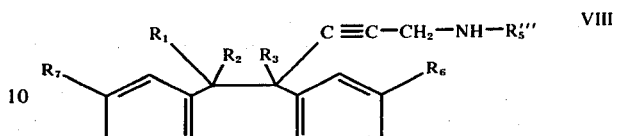

and

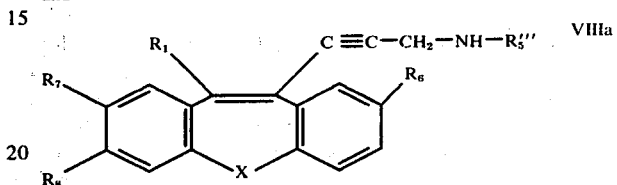

wherein $R_1$, $R_2$, $R_3$, $R_6$, $R_7$, $R_8$ and X are as hereinbefore described, $R_5'''$ is hydroxy-(lower alkyl)- except that any hydroxy group defined by $R_6$, $R_7$ and $R_8$ can also be protected, is reacted with an alkanoylating agent, or g. Convert a base of formula I or Ia or an N-oxide thereof into the corresponding pharmaceutically acceptable acid addition salt.

The compounds of formulas II, IIa, IV, IVa, V, Va, VI, VIa, VII, VIIa, VIII and VIIIa are novel and also within the scope of the invention.

The following description will further illustrate the processes for the preparation of the tricyclic compounds of the invention, as well as their salts and respectively, their pharmaceutically acceptable acid addition salts.

The starting materials of formula IIa can be prepared by the reaction of the corresponding 10-ketones with an acetylene/metal organic compound, for example, lithium acetylide, an acetylene-magnesium halide or trimethylsilylethynyl lithium. The lithium acetylide is preferably reacted in liquid ammonia and/or an organic solvent, for example, tetrahydrofuran or benzene, or as a complex with ethylene diamine in an inert organic solvent, such as dioxane, tetrahydrofuran or benzene at a temperature between about −10° C. and the boiling point of the reaction mixture. The acetylene/magnesium halide and the trimethylsilylethynyl lithium are preferably reacted in an organic solvent such as tetrahydrofuran or benzene, at a temperature between about −10° C. and the boiling point of the reaction mixture. The resulting addition product is subsequently hydrolyzed, for example, by reacting with aqueous ammonium chloride solution at room temperature. The resulting 10-ethynyl-10-carbinol or, when trimethylsilylethynyl lithium is used, the resulting 10-trimethylsilylethynyl-10-carbinol, is subsequently dehydrated, for example, by heating with a strong acid such as p-toluenesulfonic acid in an organic solvent such as methylene chloride, carbon tetrachloride, acetonitrile, benzene, o-, m- or p-xylene, whereby there is obtained the compound of formula IIa or, when trimethylsilylethynyl lithium is used, the corresponding 10-trimethylsilylethynyl compounds. These latter compounds are subjected to a metal-catalyzed hydrolysis by, for example, treatment in aqueous acetone or in aqueous ethanol with silver nitrate and potassium cyanide. The trimethylsilyl group is cleaved under these conditions, even at room temperature, and there is obtained a starting material of formula IIa.

The compounds of formula II can be prepared, for example, by the reaction of the corresponding tricyclic 10-halo compound, for example, the chloro compound, with an acetylene/metallic organic compound as described above. The reaction, preferably is carried out in an inert organic solvent such as, for example, ether, benzene or tetrahydrofuran, at a temperature between about −10° C. and the boiling point of the reaction mixture.

The preparation of the compounds of the invention from the starting materials of formulas II and IIa by reaction with formaldehyde and a compound of formula III in accordance with embodiment (a) is carried out in accordance with a Mannich reaction. Preferably, it is carried out in the presence of an inert organic solvent, for example, in the presence of a lower alkanol such as methanol or ethanol, a cyclic ether, for example, dioxane, or a lower alkanecarboxylic acid such as acetic acid; alternatively, in admixture with water. The temperature of the reaction is in the range of from about 0° to 100°. The reaction is preferably catalyzed by metal salts, especially copper (II) salts such as copper (II) acetate.

The symbol Y of the starting materials of formula IV or IV preferably is halogen or alkyl-substituted or aryl-substituted sulfonyloxy. Preferably, the substituent on the sulfonyl moiety is alkyl or aryl such as lower alkyl, especially methyl or phenyl or p-tolyl. Y as halogen is preferably chloro or bromo.

The 10,11-unsaturated compounds of formula IVa can be prepared, for example, by reacting the corresponding tricyclic 10-ketones, which are known compounds or can be prepared according to known procedures, with a metallo organic compound of 2-propynyl-2-tetrahydropyranyl ether, for example, with the corresponding lithium or magnesium halide compound. The metallo organic compound of 2-propynyl-2-tetrahydropyranyl ether carries the corresponding metal radical, for example, lithium or magnesium halide radical on the carbon in the 3-position of the 2-propynyl moiety. The lithium compound is preferably reacted in liquid ammonia and/or an organic solvent, such as, for example, tetrahydrofuran, the magnesium halide compound is reacted in an organic solvent such as tetrahydrofuran, at a temperature between about −10° C and the boiling point of the reaction mixture. The resulting addition compound is subsequently subjected to hydrolysis, for example, by treatment with aqueous ammonium chloride at room temperature, and the resulting tricyclic 10-[3-(2-tetrahydropyranyloxy)-1-propynyl]-10-carbinol is subjected to dehydration/hydrolysis, for example, by treatment with a strong acid such as p-toluenesulfonic acid, in methylene chloride, benzene or o-, m- or p-xylene at the boiling temperature of the reaction mixture, and subsequently, boiling with p-toluenesulfonic acid in aqueous ethanol, the dehydration product being thus hydrolyzed. The resulting 10,11-unsaturated, tricyclic 10-(3-hydroxy-1-propynyl) compound can now be converted to the corresponding 10,11-unsaturated reactive ester of formula IVa, for example, by reaction with the corresponding alkyl-substituted or aryl-substituted sulfonic acid halide, for example, the chloride, or with thionyl chloride or thionyl bromide. Another method for the preparation of the 10,11-unsaturated starting materials of formula IVa is described in Example 5 hereinafter.

The 10,11-saturated compound of formula IV can be prepared by reacting the corresponding tricyclic 10-halo compound, for example, the chloro compound, which are known compounds or can be prepared according to known procedures, with one of the above-mentioned metallo organic compounds of 2-propynyl-2-tetrahydropyranyl ether. The resulting 10,11-saturated, tricyclic 10-[3-(2-tetrahydro-pyranyloxy)-1-propynyl]compound can subsequently, as described above, be hydrolyzed and the corresponding 10,11-saturated reactive ester of formula IV prepared.

The reaction in accordance with the invention of a compound of formula IV or IVa and a compound of formula III can be carried out in an inert organic solvent such as benzene, toluene, dimethylformamide, or the like. Preferably, the reaction is carried out in the presence of an excess of the compound of formula III, whereby it also serves as an acid-binding agent. As other acid-binding agents in this reaction, there can be utilized, for example, anhydrous potassium carbonate. When employing a readily volatile compound of formula III, the reaction is suitably carried out in a sealed vessel at elevated temperatures, for example, at a temperature in the range of from about 50° to about 175°. The reaction temperature is not critical. Expediently, it is in the range of from about −20°C. to about the boiling point of the reaction mixture; preferably, between room temperature and the boiling point of the reaction mixture.

The tricyclic 10-carbinols of formula V can be prepared, for example, by the reaction of the corresponding tricyclic 10-ketones, which are known compounds or can be prepared according to known procedures, with a metallo organic compound of the correspondingly substituted 2-propynylamine which may be N-substituted. For example, there can be reacted the corresponding lithium or magnesium halide compound; the metal radical is in the 3-position of the 2-propynylamine. Lithium compounds are preferably reacted in liquid ammonia and an organic solvent such as tetrahydrofuran; magnesium halogen compounds are reacted in an organic solvent such as tetrahydrofuran, at the boiling point of the reaction mixture. The resulting addition compound is subsequently subjected to hydrolysis, for example, by treatment with aqueous ammonium chloride at room temperature, whereby the corresponding tricyclic carbinol of formula V is obtained.

The 11-carbinols of formula V can be prepared, for example, by the reaction of a tricyclic 10,11-epoxide, which are known compounds or can be prepared according to known procedures, with the above-described metallo organic compound of the correspondingly substituted 2-propynylamine. The lithium compound is preferably reacted in liquid ammonia and an organic solvent such as tetrahydrofuran; the magnesium halide is preferably reacted in an organic solvent such as tetrahydrofuran at the boiling point of the reaction mixture. This method is particularly well suited for the preparation of symmetrically substituted starting materials of formula V, for example, the 2,8-dichloro or the 2,8-dimethyl compounds. The utilization of unsymmetrically substituted 10,11-epoxides results in a mixture of steroisomers, for example, in a mixture of 2-substituted and 8-substituted compounds which can be separated according to known methods, for example, by column chromatography.

The dehydration of the starting materials of formula V in accordance with embodiment (c) of the invention leads to the 10,11-unsaturated compounds of formula Ia. The dehydration can be carried out suitably by utilizing a strong acid, for example, an organic sulfonic acid, such as p-toluenesulfonic acid, methane-sulfonic acid or a mineral acid such as hydrochloric or hydrobromic acid, in an aqueous or non-aqueous medium. Preferably, the dehydration is carried out in an organic sulfonic acid, for example, p-toluenesulfonic acid, in the presence of an inert organic solvent, such as methylene chloride, carbon tetrachloride, acetonitrile, benzene or o-, m- or p-xylene. When utilizing a mineral acid, this is carried out, for example, in solution in a lower alkanol. The dehydration can also be carried out by heating in a high-boiling non-aqueous solvent such as dimethylsulfoxide. Other known dehydrating agents can likewise be utilized, for example, acetic anhydride. The temperature for the dehydration preferably is in the range of from about 50° to about 200°.

For the alkylation of the compounds of formula Vi or formula Via in accordance with embodiment (d) of the process of the invention, several methods are available.

In case a tertiary amine of formula I or Ia is desired, it can be prepared, for example, as follows:

A starting material of formula VI or VIa, respectively, is reacted with a compound of the formula
$$R'_5, Y_1$$
wherein $R'_5$ is lower alkyl and $Y_1$ is a leaving group, for example, halogen such as chlorine, bromine or iodine or lower alkanesulfonyloxy, benzenesulfonyloxy or lower alkylbenzenesulfonyloxy.

As the alkylating agent, there can also be used ethylene oxide, which may be substituted by lower alkyl and in this manner, there is introduced hydroxyethyl which may be substituted by lower alkyl. The reaction preferably is carried out in an inert solvent, for example, a lower alkanol such as ethanol, or dimethylformamide, at a temperature in the range of from about 15° to about 75°.

In another process for the preparation of the tertiary amines of formula I or Ia, a starting material of formula VI or VIa, respectively, is reacted with a mixture of formaldehyde and formic acid, preferably in an excess at an elevated temperature, for example, at a temperature in the range of from about 50° to about the boiling point of the reaction mixture. Instead of formic acid, sodium borohydride can be utilized in this reaction.

The starting materials of formulas VI and VIa, wherein $R'_4$ is hydrogen, that is, primary amines of formula VI or VIa, can be converted into secondary amines of formula I or Ia by reacting a primary amine of formula VI or VIa, respectively, with a haloformic acid ester, for example, chloroformic or bromoformic acid ethyl ester, to form a carbamate; the carbamate is subsequently reduced with a complex metal hydride, for example, lithium aluminum hydride. Both reaction steps are preferably carried out in an inert solvent, for example, in ether or tetrahydrofuran, at a temperature in the range of from about room temperature to the reflux temperature of the reaction mixture, especially at the reflux temperature.

In another process for preparing the secondary amines of formula I or Ia, a primary amine of formula VI or VIa, respectively, is reacted with chloral, preferable in an inert solvent such as chloroform or benzene, at an elevated temperature, for example, at a temperature in the range of between about 50° and the boiling point of the reaction mixture. The resulting formylamino compound is subsequently reduced with a complex metal hydride, for example, lithium aluminum hydride, in anhydrous ether to a secondary amine corresponding to formula I or Ia.

In another method for preparing the secondary amines of formula I or Ia, a primary amine of formula VI or VIa, respectively, is reacted with formaldehyde, preferably in an inert solvent, for example, benzene or toluene, at a temperature in the range of from about room temperature and the boiling point of the reaction mixture. The resulting Schiff's base is subsequently converted to a secondary amine of formula I or Ia reduction. The reduction is suitably carried out by treatment of the Schiff's base with a complex metal hydride such as sodium borohydride or lithium aluminum hydride in anhydrous ether or dioxane.

The oxidation, according to embodiment e) of the process aspects of the invention, of a compound of formula VII or VIIa results in the corresponding N-oxide. As the oxidizing agent, preferably hydrogen peroxide or an organic peracid, for example, m-chloroperbenzoic acid, is used. Advantageously, the oxidation is carried out in an inert organic solvent, for example, in a lower alkanol such as methanol or ethanol, ether, benzene, chloroform or methylene chloride, at a temperature in the range of from about −50° C. to about room temperature, preferably at a temperature between about 0° C. and room temperature. After removal of the excess oxidizing agent and work-up according to known procedures, there is obtained the corresponding N-oxide. The latter can then be converted, conveniently, into a pharmaceutically acceptable acid addition salt.

The alkanoylation of a compound of formula VIII or VIIIa in accordance with embodiment f) of the process aspects of the invention can be carried out conveniently by heating at a temperature in the range of from about 50° to about 150° with a reactive derivative of the corresponding alkanecarboxylic acid, for example, the corresponding acid chloride or acid anhydride. The esterification can also be carried out by reaction with an alkanecarboxylic acid in the presence of a strong acid catalyst, for example, sulfuric acid or p-toluenesulfonic acid, or in the presence of of a dehydrating agent, for example, dicyclohexylcarbodiimide or carbonyldiimidazole. The esterification is preferably carried out in an organic solvent, for example, benzene, toluene or pyridine.

If it is desired to prepare a compound of formula I or Ia, wherein $R_6$ and, if desired, $R_7$ and/or $R_8$, is hydroxy, or a corresponding N-oxide, there is preferably used a starting material of formula II, IIa, V, Va, VI, VIa, VII, VIIa, VIII or VIIIa, respectively, in which the hydroxy group is protected, for example, by a lower alkyl, benzyl or trimethylsilyl group. After completion of any desired reaction, the protecting group is cleaved. An alkyl group is preferably cleaved by treatment with a pyridine salt, for example, pyridine hydrochloride, if necessary in the presence of water, or by treatment with a boron trihalide, for example, boron tribromide or boron trichloride; a benzyl group is preferably cleaved in a manner similar to that described for the cleavage of a lower alkyl group or by treatment with an alkali metal, such as sodium, in a lower alkanol, such as butanol; and a trimethylsilyl group is preferably cleaved by acid-catalyzed hydroysis, for example, by treatment with aqueous-alcoholic mineral acid such as aqueous ethanolic hydrochloric acid. The cleavage is preferably carried out in an inert organic solvent, for example, benzene, toluene, xylene, or a halogenated hydrocarbon, such as methylene chloride, chloroform or carbon tetrachloride, at a temperature in the range of from about room temperature to about the boiling point of the mixture, except that when a boron trihalide is utilized in the cleavage reaction, the temperature conveniently is in the range of from about −70° C. to about room temperature.

The obtained bases of formulas I and Ia form salts with inorganic as well as organic acids, for example, with hydrohalic acids such as hydrochloric acid, hydrobromic acid or hydroiodic acid, with other mineral acids such as sulfuric acid, phosphoric acid or nitric acid; also with organic acids such as tartaric and acetic acid, citric acid, camphorsulfonic acid, methanesulfonic acid, toluenesulfonic acid, ascorbic acid, maleic acid, mandelic acid and the like. Preferred salts are those formed with hydrohalic acid. Especially preferred are those formed with hydrochloric acid and maleic acid. The pharmaceutically acceptable acid addition salts, preferably, can be prepared in an inert solvent, for example, ethanol, acetone, acetonitrile, by treating the free base with the corresponding anhydrous acid.

The bases of formulas I and Ia are partly crystalline, solid substances which are relatively soluble in dimethylsulfoxide, dimethylformamide, or in chlorinated hydrocarbons such as chloroform, methylene chloride, or in a alkanol such as methanol or ethanol, and are relatively insoluble in water.

The pharmaceutically acceptable acid addition salts of the bases of formulas I and Ia are crystalline, solid substances. They are freely soluble in dimethylsulfoxide and dimethylformamide, in an alkanol such as methanol or ethanol, and also in chloroform, methylene chloride and water. The pharmaceutically acceptable addition salts of the bases of formulas I and Ia are relatively insoluble in benzene, ether and petroleum ether.

The compounds of formulas I and Ia are useful as neuroleptic agents, substantaily devoid of cataleptic activity or effect.

A cataleptic effect (wax-like rigidity, that is, maintaining for an abnormally long period a forced upon body position) is considered to be a disturbing side effect with neuroleptically active compounds and indicates motor disturbances. The products according to the invention have the advantage that they do not have this disturbing side effect or have it only to a very slight extent. To prove the lack of cataleptic activity, representative samples of the end products of the invention were administered intraperitoneally to rats. The following compounds were tested:

Product A: N,N-dimethyl-3-[8-(methylthio)-dibenzo[b,f]thiepin-10-yl]-2-propynylamine maleate;

Product B: N,N-dimethyl-3-(8-chloro-dibenzo[b,f]thiepin-10-yl)-2-propynylamine maleate;

Product C: N,N-dimethyl-3-(8-chloro-3-methoxydibenzo[b,f]thiepin-10-yl)-2-propynylamine methanesulfonate.

The foregoing compounds were compared to chlorpromazine, a well-known central depressant, especially well-known as a neuroleptic agent. The test animals are considered to be cataleptic when the homolateral extremities remain in the crossed position for at least 10 seconds. The number of cataleptic animals is recorded every 30 minutes over a 6-hour period. The $ED_{50}$ is the dose at which 50% of the animals are cataleptic.

| Test Substance | RESULTS: $ED_{50}$ mg/kg. |
| --- | --- |
| N,N-dimethyl-3-[8-(methylthio)-dibenzo[b,f]-thiepin-10-yl]-2-propynylamine maleate (Product A) | >100 |
| N,N,-dimethyl-3-(8-chloro-dibenzo[b,f]-thiepin-10-yl)-2-propynylamine maleate (Product B) | 100 |
| N,N-dimethyl-3-(8-chloro-3-methoxy-dibenzo[b,f]-thiepin-10-yl)-2-propynylamine methane-sulfonate (Product C) | >100 |
| Chlorpromazine | 6 |

The table demonstrates that no or, respectively, very weak cataleptic effect is produced by Substances A, B and C in comparison to chlorpromazine, which does demonstrate cataleptic effects.

The demonstrate the neuroleptic effect of the products of the invention, representative compounds are utilized in the following tests:

I. Determination of Homovanillinic Acid

Two hours prior to being killed, rats are injected with the test substance.

Thereafter, the homovanillinic acid is extracted from the supernatant portion of a homogenized mixture of brains of the treated rats into butylacetate and later into an aqueous solution and is oxidized with potassium ferric cyanide to a fluorescent dimer. From an increased concentration of homovanillinic acid, (HVA). it can be demonstrated that the test substance words that same as chlorpromazine, that is, it increases the turnover of dopamine in the basal ganglions. The homovanillinic titer in untreated rats is arbitrarily set at 100%.

A comparison between Substance A, B and C and chlorpromazine gave the following results:

| Test Substance | RESULTS: Dose mg/kg. p.o. | Increase of HVA % |
| --- | --- | --- |
| N,N-dimethyl-3-[8-(methylthio)-dibenzo[b,f]thiepin-10-yl]-2-propynylamine maleate (Product A) | 50 | 330 |

| -continued RESULTS: | | |
|---|---|---|
| Test Substance | Dose mg/kg. p.o. | Increase of HVA % |
| N,N-dimethyl-3-(8-chloro-dibenzo[b,f]-thiepin-10-yl)-2-propynylamine maleate (Product B) | 50 | 370 |
| N,N-dimethyl-3-(8-chloro-3-methoxy-dibenzo[b,f]thiepin-10-yl)-2-propynylamine methanesulfonate (Product C) | 30 | 320 |
| Chlorpromazine | 20 | 321 |

The compounds of the invention, i.e., the compounds of formulas I and Ia, can be used in the form of pharmaceutical preparations, which contain them or their salts, in admixture with organic or inorganic pharmaceutically inert carriers suitable for enteral or parenteral application such as, for example, water, gelatin, milk sugar, starch, magnesium stearate, talc, vegetable oils, gum arabic, polyalkyleneglycols and the like. The pharmaceutical preparations can be in solid form, for example, tablets, dragees, suppositories, capsules or in liquid form, for example, as solution, suspensions, or emulsions. The preparation may be sterilized and/or contain additives such as preservatives, stabilizers, wetting or emulsifying agents, or salts for varying the osmotic pressure. The pharmaceutical preparations can also contain additional therapeutically active substances.

Preferably, the pharmaceutical dosage forms contain from about 1 to about 200 mg. of a compound of formula I or Ia or an equivalent amount of its salts. Preferably, the oral dosage range is between about 0.1 mg/kg/day to about 7.5 mg/kg/day. A preferable dosage range for parenteral preparations is in the range of from about 0.01 mg/kg/day to about 0.75 mg/kg/day. It is understood, however, that the above-mentioned ranges can be varied according to the individual needs and prescription of the practitioner.

As is evidnet, the compounds of formulas I and Ia and their pharmaceutically acceptable acid addition have effects qualitatively similar to those of chlorpromazine, known for its therapeutic uses and properties. Thus, the compounds of the invention demonstrate a pattern of activity associated with neuroleptic agents of known efficacy and safety.

The following examples further illustrate the invention. All temperatures are in degrees Centigrade, unless otherwise mentioned.

EXAMPLE 1

Preparation of N,N-dimethyl-3-(8-chloro-dibenzo [b,f] thiepin-10-yl)-2-propynylamine 63 G. of p-toluenesulfonic acid and 1,800 ml. of o-xylene are heated to boiling and the water present is distilled. The solution is reacted with 90 g. of 10-[3-(dimethylamino)-1-propynyl]-8-chloro-10,11-dihydro-dibenzo[b,f]thiepin-10-ol. The reaction mixture is maintained at the boiling temperature for 45 minutes, whereby the remaining water is distilled. The mixture is cooled and poured into 90 ml. of 2N aqueous sodium hydroxide. The aqueous phase is extracted with ether. The resulting organic phase is washed three times with water and subsequently extracted three times with aqueous methanesulfonic acid. The aqueous phase is washed with water and made alkaline with concentrated sodium hydroxide. The reaction mixture is then extracted with ether, and the ether extract washed with water, dried and evaporated, whereby there is obtained N,N-dimethyl-3-(8-chloro-dibenzo[b,f,]thiepin-10-yl)-2-propynylamine, which after recrystallization from hexane, has a melting point of 118°-120° C. The maleate is precipitated from ethanol and melts at 178°-½°.

The starting material 10-[3-(dimethylamino)-1-propynyl]-8-chloro-10,11-dihydro-dibenzo[b,f,]thiepin-10-ol can be prepared as follows:

2100 Ml. of liquid ammonia is reacted with some crystalline ferric nitrate and subsequently with 10.4 g. of lithium metal over a 2-hour period. After stirring for 30 minutes, there are added 369 ml. of dimethylamino-1-propyne over a 40-minute period, and the reaction mixture is stirred for an additional 45 minutes. Over a 105-minute period, there is added dropwise a solution of 300 g. of 8-chloro-10,11-dihydro-5H-dibenzo [b,f]thiepin-10-one in 1500 ml. of tetrahydrofuran. The reaction mixture is allowed to stand overnight. The following morning, the reaction mixture is treated with 228 g. of ammonium chloride in 600 ml. of water. The ammonia, thereafter, is evaporated. 900 Ml. of tetrahydrofuran are added, and the mixture is heated at reflux for 2 hours. The reaction mixture is evaporated, diluted with water and extracted with ether. The ether extract is washed with water and extracted three times with aqueous methanesulfonic acid. The unreacted starting ketones can be recovered from the ethereal phase. The aqueous phase is made alkaline with concentrated sodium hydroxide, whereby there is obtained 10-[3-(dimethylamino)-1-propynyl]-8-chloro-10,11-dihydrodibenzo[b,f,]thiepin-10-ol, which is taken up in chloroform. The chloroform phase is washed with water, dried and evaporated, whereby there is obtained the above-named product, which after recrystallization from acetone, has a melting point of 150°-152°.

EXAMPLE 2

In a similar manner to that described in Example 1, from 10-[3-(dimethylamino)-1-propynyl]-10,11-dihydro-8-(methylthio)-dibenzo[b,f]thiepin-10-ol, there is obtained N,N-dimethyl-3-[8-(methylthio)-dibenzo[b,f]thiepin-10-yl]propynylamine. The maleate of the product has a melting point of 145°-146°.

The starting material can be prepared in an analogous manner to that described in Example 2, from 10-11-dihydro-8-(methylthio)-5H-dibenzo [b,f]thiepin-10-one and after recrystallization from benzene/-hexane, has a melting point of 142°-144°.

EXAMPLE 3

In a similar manner to that described in Example 1, from 10-[3-(dimethylamino)-1-propynyl]-10,11-dihydro-8-methyl-dibenzo[b,f]thiepin-10-ol, there is obtained N,N-dimethyl-3(8-methyl-dibenzo[b,f]thiepin- 10-yl)-2-propynylamine. The latter compound can be purified by chromatography on silica gel with chloroform as the eluant solution. The corresponding maleate melts at 121–123°.

The starting material can be prepared in an analogous manner to that described in Example 1, from 10-11-dihydro-8-methyl-5H-dibenzo [b,f]thiepin-10-one and melts after recrystallization from ether, at 145°–147.5°.

EXAMPLE 4

Preparation of N,N-dimethyl-3-[8-chloro-dibenzo [b,f]-thiepin-10-yl]-2-propynylamine A solution of 5.1 g. of 10-ethynyl-8-chloro-dibenzo [b,f]-thiepin in 40 ml. of absolute dioxane is treated with 630 mg. of paraformaldehyde, 4.5 ml. of a 6-M solution of dimethylamine in dioxane and 200 mg. of copper (II) acetate. The mixture is heated at 100° C. in a well-sealed flask for 2 hours. After cooling, the mixture is poured onto ice and then acidified with 3-N methanesulfonic acid. The neutral products are removed by extraction with ether. The aqueous phase is made alkaline with ammonia. By extraction with ether, there is obtained N,N-dimethyl-3-[8-chloro-dibenzo[b,f]thiepin-10-yl)]-2-propynylamine, which melts at 118°–120° C. after recrystallization from hexane. The maleate melts at 178°–180° C.

In an analogous manner to that described above, the following compounds are prepared:

N,N-dimethyl-3-[8-methylthio-dibenzo[b,f]thiepin-10-yl]-2-propynylamine; melting point 78°–80° C. The hydrochloride salt melts at 182°–184° C;

N,N-dimethyl-3-[8-methyl-dibenzo[b,f]thiepin-10-yl]-2-propynylamine; melting point 70°–72° C. The hydrochloride salt melts at 214°–216° C.

N,N-dimethyl-3-[8-fluoro-dibenzo[b,f]thiepin-10-yl]-2-propynylamine; melting point 59°–61° C. The hydrochloride salt melts at 234°–236° C;

N,N-diethyl-3-[8-chloro-dibenzo[b,f]thiepin-10-yl]-2-propynylamine. The maleate salt melts at 146°–148° C;

N,N-dimethyl-3-[8-chloro-2-methyl-dibenzo[b,f]-thiepin-10-yl]-2-propynylamine; melting point 96°–97° C. The hydrochloride salt melts at 174°–176° C;

1-[3-(8-chloro-dibenzo[b,f]thiepin-10-yl)-2-propynyl]-piperidine; melting point 59°–61° C. The methanesulfonate salt melts at 179°–181° C;

4-[3-(8-chloro-dibenzo[b,f]thiepin-10-yl)-2-propynyl]-morpholine, melting point 109° C. The methanesulfonate salt melts at 164°–166° C;

1-[3-(8-chloro-dibenzo[b,f]thiepin-10-yl)-2-propynyl]-pyrrolidine; melting point 76°–77° C. The methanesulfonate salt melts at 152°–154° C;

N,N-dimethyl-3-[8-fluoro-2-methyl-dibenzo[b,f]-thiepin-10-yl]-2-propynylamine; melting point 74°–76° C. The hydrochloride salt melts at 231°–234° C;

N,N-dimethyl-3-[8-chloro-3-methoxy-dibenzo[b,f]-thiepin-10-yl]-2-propynylamine; melting point 102°–104° C. The methanesulfonate salt melts at 211°–214° C;

N,N-dimethyl-3-[8-methoxy-dibenzo[b,f]thiepin-10-yl]-2-propynylamine; melting point 68°–71° C. The methanesulfonate salt melts at 132°–135° C;

N,N-dimethyl-3-[8-chloro-dibenzo[b,f]oxepin-10-yl]-2-propynylamine; melting point 62°–64° C. The methanesulfonate salt melts at 127°–129° C;

N,N-dimethyl-3-[8-isopropyl-dibenzo[b,f]thiepin-10-yl]-2-propynylamine; boiling point 170° C/0.02 mm Hg. The hydrochloride salt melts at 194°–197° C;

N,N-dimethyl-3-[2,8-dichloro-dibenzo[b,f]thiepin-10-yl]-2-propynylamine; melting point 83°–85° C. The hydrochloride salt melts at 224°–227° C;

2-{[3-(8-chloro-dibenzo[b,f]thiepin-10-yl)-2-propynyl]-methylamino}-ethanol; melting point 87°–90° C. The maleate salt melts at 149°–151° C;

2-{4-[3-(8-chloro-dibenzo[b,f]thiepin-10-yl)-2-propynyl]-1-piperazinyl}ethanol; melting point 111°–113° C. The dihydrochloride salt melts at 253°–257° C;

N,N-dimethyl-3-[2-chloro-8-methylthio-dibenzo[b,f]thiepin-10-yl]-2-propynylamine; melting point 100°–103° C. The hydrochloride salt melts at 206°–208° C;

N,N-dimethyl-3-[2-methyl-8-methylthio-dibenzo[b,f]thiepin-10-yl]-2-propynylamine; melting point 80°–82° C. The hydrochloride salt melts at 185°–187° C;

N,N-dimethyl-3-[8-nitro-dibenzo[b,f]thiepin-10-yl]-2-propynylamine; melting point 113 –115° C. The maleate salt melts at 179°–182° C;

N,N-dimethyl-3-[8-chloro-11-methyl-dibenzo[b,f]-thiepin-10-yl]-2-propynylamine; boiling point 210° C/0.2 mm Hg. The hydrochloride salt melts at 240°–243° C;

N,N-3-[3-methyl-8-methylthio-dibenzo[b,f]thiepin-10-yl]-2-propynylamine; melting point 69°–72° C. The maleate salt melts at 161°–163° C;

N,N-dimethyl-3-[8-amino-dibenzo[b,f]thiepin-10-yl]-2-propynylamine;

N,N-dimethyl-3-[8-dimethylamino-dibenzo[b,f]thiepin-10-yl]-2-propynylamine;

N,N-dimethyl-3-[8-methylfulfonyl-dibenzo[b,f]thiepin-10-yl]-2-propynylamine; melting point 131°–133° C. The hydrochloride salt melts at 247°–250° C;

N,N-dimethyl-3-[8-dimethylsulfamoyl-dibenzo[b,f]-thiepin-10-yl]-2-propynylamine; melting point 112°–114° C. The hydrochloride salts melts at 217°–220° C;

N,N-dimethyl-3-[8-trifluoromethyl-dibenzo[b,f]thiepin-10-yl]-2-propynylamine; melting point 88°–91° C. The hydrochloride salt melts at 196°–198° C.

The 10-ethynyl-8-chloro-dibenzo[b,f]thiepin used as the starting material for the preparation of N,N-dimethyl-3-(8-chloro-dibenzo[b,f]thiepin-10-yl)-2-propynylamine can be prepared as follows:

56 G. of a trimethylethynylsilane/tetrahydrofuran mixture (corresponding to 0.44 mole of trimethylethynylsilane) in 300 ml. of benzene are slowly treated dropwise at 0° C. with 235 ml. of n-butyllithium solution in hexane (corresponding to 0.4 mole). After stirring for an additional 0.5 hour at this temperature, a solution of 52.8 g. of 8-chloro-10,11-dihydro-5H-dibenzo[b,f]thiepin-10-one in 250 ml. of benzene is slowly added dropwise. The solution is left overnight in a refrigerator. On the following morning, the mixture is poured onto a solution comprising 250 g. of ammonia chloride in 1.5 liters of water. By extraction with benzene, there is obtained a mixture of unreacted starting ketone [i.e., 8-chloro-10,11-dihydro-5H-dibenzo[b,f]- thiepin-10-one]and 8-chloro-10,11-dihydro-10-(trimethylsilylethynyl)-dibenzo[b,f]thiepin-10-ol which is subjected directly to a water-cleavage step.

For this purpose, the mixture is taken up in 500 ml. of benzene and, after the addition of 1.2 g. of p-toluenesulfonic acid, boiled for 2 hours at reflux, the resulting water is removed by distillation. By dilution with benzene and washing to neutrality with water, there is obtained a mixture of unreacted starting ketone and [(8-chloro-dibenzo[b,f]thiepin-10-yl)-ethynyl]-trimethylsilane which is treated to cleave the trimethylsilyl group.

To the latter mixture, which has been dissolved in 660 ml. of acetone/water (10:1), there is added dropwise over a period of 30 minutes a solution of 64 g. of silver nitrate in 150 ml. of water, and the mixture is stirred for an additional 1 hour. Then, a solution of 120 g. of potassium cyanide in 500 ml. of water and 500 ml of benzene is added and the mixture stirred until two clear phases result. By extraction with benzene, there is obtained a mixture of unreacted starting ketone and 10-ethynyl-8-chloro-dibenzo[b,f]thiepin which is separated by chromatography on silica gel. The 10-ethynyl-8-chloro-dibenzo[b,f]thiepin melts at 105°–108° C. after recrystallization from ether/n-pentane.

In an analogous manner to that described above, the following starting materials are prepared:

10-ethynyl-8-methylthio-dibenzo[b,f]thiepin; melting point 99°–101° C;
10-ethynyl-8-methyl-dibenzo[b,f]thiepin; melting point 94°–96° C;
10-ethynyl-8-fluoro-dibenzo[b,f]thiepin; oil (pure according to thin-layer chromatography);
10-ethynyl-8-chloro-2-methyl-dibenzo[b,f]thiepin; melting point 127°–129° C;
10-ethynyl-8-fluoro-2-methyl-dibenzo[b,f]thiepin; melting point 74°–76° C;
10-ethynyl-8-chloro-3-methoxy-dibenzo[b,f]thiepin; melting point 103°–105° C;
10-ethynyl-8-methoxy-dibenzo[b,f]thiepin; melting point 131°–136° C;
10-ethynyl-8-chloro-dibenzo[b,f]oxepin; melting point 118°–120° C;
10-ethynyl-8-isopropyl-dibenzo[b,f]thiepin; oil (pure according to thinlayer chromatography);
10-ethynyl-2,8-dichloro-dibenzo[b,f]oxepin; melting point 134°–137° C;
10-ethynyl-2-chloro-8-methylthio-dibenzo[b,f]thiepin; melting point 100°–103° C; 10-ethyl-2-methyl-8-methylthio-dibenzo[b,f]thiepin; melting point 124°–126° C;
10-ethynyl-8-nitro-dibenzo[b,f]thiepin; melting point 175–177° C;
10-ethynyl-8-chloro-11-methyl-dibenzo[b,f]thiepin; oil (pure according to thin-layer chromatography);
10-ethynyl-3-methyl-8-methylthio-dibenzo[b,f]thiepin; oil (pure according to thin-layer chromatography);
10-ethynyl-8-methylsulfonyl-dibenzo[b,f]thiepin; melting point 140–143° C; 10-ethynyl-8-aminodibenzo[b,f]thiepin;
10-ethynyl-8-dimethylamino-dibenzo[b,f]thiepin;
10-ethynyl-8-dimethylsulfamoyl-dibenzo[b,f]thiepin; melting point 133°–135° C; and
10-ethynyl-8-trifluoromethyl-dibenzo[b,f]thiepin; melting point 63–65° C.

EXAMPLE 5

Preparation of N-methyl-3-(8-chloro-dibenzo[b,f]thiepin-10-yl)-2-propy-nylamine

A mixture of 20 ml. of dimethylformamide and 10 ml. of methylamine is slowly treated dropwise at about 0° C. with a solution of 4.7 g. of 3-(8-chloro-dibenzo[b,f]thiepin-10-yl)-2-propynyl-1-ol mesylate in 30 ml. of dimethylformamide. After about 1 hour, the mixture is poured onto water. By extraction with ether, there is obtained N-methyl-3-(8-chloro-dibenzo[b,f]-thiepin-10-yl)-2-propynylamine which melts at 92–94° C. after recrystallization from ether. The maleate salt melts at 104°–106° C.

In an analogous manner to that described above, the following compound is prepared:

3-(8-chloro-dibenzo[b,f]thiepin-10-yl)-2-propynlamine; melting point of the maleate salt is 170°–172° C.

The 3-(8-chloro-dibenzo[b,f]thiepin-10-yl)-2-propyn-1-ol mesylate used as the starting material for the preparation of N-methyl-3-(8-chloro-dibenzo[b,f]-thiepin-10-yl)-2-propynylamine can be prepared as follows:

A solution of 13.5 g. of 10-ethynyl-8-dibenzo[b,f]-thiepin in 150 ml. of absolute tetrahydrofuran is treated dropwise at room temperature with 52 ml. of a 1-M solution of ethylmagnesium bromide solution in tetrahydrofuran. After stirring the mixture for an additional hour, 1.85 g. of paraformaldehyde are pyrrolyzed and led through the mixture in gaseous form. The solution, having now warmed to about 50° C., is stirred for an additional 30 minutes and then poured onto a saturated, aqueous ammonium chloride solution. By extraction with benzene and subsequent chromatography on silica gel using benzene/methanol (20:1) as the eluent, there is obtained 3-(8-chloro-dibenzo[b,f]thiepin-10-yl)-2-propyn-1-ol which melts at 111°–113° C. after recrystallization from ethyl acetate/petroleum ether.

A solution of 6 g. of 3-(8-chloro-dibenzo[b,f]thiepin-10-yl)-2-propyn-1-ol in 50 ml. of pyridine is treated dropwise at −10° C. to 0° C. with 1.7 ml. of methanesulfonyl chloride in 10 ml. of pyridine and stirred at this temperature for 2 hours. After pouring onto ice, acidification with hydrochloric acid and extraction with eher, there is obtained 3-(8-chloro-dibenzo[b,f]thiepin-10-yl)-2-propyn-1-ol mesylate which melts at 100°–102° C. after recrystallization from ether.

EXAMPLE 6

Preparation of 2-{[3-(8-chloro-dibenzo[b,f]thiepin-10-yl)-2propynyl]-methylamino}-ethanol A solution of 2 ml. of ethylene oxide in 10 ml. of ethanol is treated with a solution of 0.6 g. of N-methyl-3-(8-chloro-dibenzo[b,f]thiepin-10-yl)-2-propynylamine in 5 ml. of ethanol and stirred at room temperature for about 4 hours. The solvent is evaporated and the residue partitioned between water and ether. The ethereal phase is washed with a dilute aqueous ammonia solution, dried over sodium sulfate and evaporated, whereby there is obtained 2-{[3-(8-chloro-dibenzo[b,f]thiepin-10yl)-2-propynyl]-methylamino}-ethanol which melts at 86–88° C. after recrystallization from ether/n-pentane.

EXAMPLE 7

Preparation of 2-{4-[3-(8-chloro-dibenzo [b,f]thiepin-10-yl)-2-propynyl]-1-piperazinyl}-ethyl acetate A solution of 5.0 g. of 2-{4-[3-(8-chloro-dibenzo[b,f]thiepin-10-yl)-2-propynyl]-1-piperazinyl}-ethanol in 50 ml. of acetic anhydride is heated for 15 minutes on a steam-bath. After evaporation of the excess acetic anhydride under greatly reduced pressure, the resulting oil is taken up in ether and washed with saturated sodium bicarbonate solution. By concentration of the ethereal phase, there is obtained 2-{4-[3-(8-chloro-dibenzo[b,f]thiepin-10-yl)-2-propynyl]-1-piperazinyl}-ethyl acetate which melts at 96°–99° C. after recrystallization from ethyl acetate/hexane.

In an analogous manner to that described above, there is obtained 2-{[3-(8-chloro-dibenzo [b,f]thiepin-10-yl)-2-propynyl]-methylamino}-ethyl acetate which melts at 48°–51° C. after recrystallization from petroleum ether.

EXAMPLE 8

Preparation of N,N-dimethyl-3-(8-chloro-dibenzo [b,f]thiepin-10-yl)-2-propynylamine N-oxide A solution of 2 g. of N,N-dimethyl-3-(8-chloro-dibenzo [b,f]thiepin-10-yl)-2-propynylamine in 100 ml. of chloroform is treated at −50° C. with 1.2 g. of m-chloroperbenzoic acid. The solution is stirred for 15 minutes at this temperature, warmed to room temperature and chromatographed on basic aluminum oxide using chloroform/methanol (9:1) as the eluant, whereby there is obtained N,N-dimethyl-3-(8-chloro-dibenzo [b,f]thiepin-10-yl)-2-propynylamine N-oxide, which melts at 68°–69° C. after recrystallization from ethyl acetate/petroleum ether.

The following Examples illustrate pharmaceutical preparations containing the tricyclic compounds provided by the invention:

EXAMPLE 9

Tablets of the following composition are prepared:

Example 9

| Tablets of the following composition are prepared: | Per Tablet |
|---|---|
| N,N-dimethyl-3-[8-(methylthio)-dibenzo-[b,f]thiepin-10-yl]-2-propynylamine maleate | 25.00 g. |
| Lactose | 110.00 g. |
| Maize Starch | 61.00 g. |
| Talc | 3.40 g. |
| Magnesium Stearate | 0.60 g. |
| | 200.00 g. |

The ingredients are mixed together and tablets of 200 mg. each are pressed. Thereafter, if desired, the tablets can be coated with ethylcellulose and Carbowax.

EXAMPLE 10

Example 10

| Tablets of the following composition are prepared: | Per Tablet |
|---|---|
| N,N-dimethyl-3-[8-(methylthio)-dibenzo-[b,f]thiepin-10-yl]-2-propynylamine | 100.0 g. |
| Lactose | 202.0 g. |
| Maize Starch | 80.0 g. |
| Hydrolyzed maize starch | 20.0 g. |
| Calcium stearate | 8.0 g. |
| | 410.0 g. |

The active ingredient, lactose, maize starch and hydrolyzed maize starch are mixed together and granulated with water to a viscous paste. This paste is passed through a sieve and subsequently dried overnight at 45° C. Thereafter, the dried granulate is passed through a sieve and mixed with the calcium stearate. The mixture obtained is pressed to tablets weighing 410 mg. and having a diameter of about 10 mm.

EXAMPLE 11

Example 11

| Tablets of the following composition are prepared: | Per Tablet |
|---|---|
| N,N-dimethyl-3-[8-(methylthio)-dibenzo-[b,f]thiepin-10-yl]-2-propynylamine | 25.0 g. |
| Lactose | 114.0 g. |
| Maize Starch | 50.0 g. |
| Gelatinized maize starch | 8.0 g. |
| Calcium stearate | 3.0 g. |
| | 200.0 g. |

The active ingredient, lactose, maize starch and gelatinized maize starch are intimately mixed with one another. The mixture is passed through a comminuting machine and subsequently moistened with water to give a thick paste. The moist mass is passed through a sieve, and the resulting moist granulate is dried at 45° C. The dried granulate is mixed thoroughly with the calcium stearate, and thereafter, pressed to tablets weighing 200 mg. and having a diameter of about 8 mm.

EXAMPLE 12

Example 12

| Tablets of the following composition are prepared: | Per Tablet |
|---|---|
| N,N-dimethyl-3-[8-(methylthio)-dibenzo-[b,f]thiepin-10-yl]-2-propynylamine maleate | 14.5 g. |
| Lactose | 124.5 g. |
| Maize Starch | 50.0 g. |
| Gelatinized maize starch | 8.0 g. |
| Calcium stearate | 3.0 g. |
| | 200.0 g. |

The active ingredient, lactose, maize starch and gelatinized maize starch are intimately mixed with one another. The mixture is passed through a comminuting machine and subsequently moistened with water to give a thick paste. The moist mass is passed through a sieve, and the resulting moist granulate is dried at 45° C. The dried granulate is mixed thoroughly with the calcium stearate, and thereafter, pressed to tablets weighing 200 mg. and having a diameter of about 8 mm.

EXAMPLE 13

Example 13

| Capsules of the following composition are prepared: | |
|---|---|
| | Per Capsule |
| N,N-dimethyl-3-[8-(methylthio)-dibenzo-[b,f]thiepin-10-yl]-2-propynylamine maleate | 29.0 g. |
| Lactose | 156.0 g. |
| Maize Starch | 30.0 g. |
| Talc | 5.0 g. |
| | 220.0 g. |

The active ingredient, lactose and maize starch are mixed intimately with one another and passed through a comminuting machine. The mixture is now mixed thoroughly with the talc and filled into hard gelatin capsules.

EXAMPLE 14

Example 14

| Capsules of the following composition are prepared: | |
|---|---|
| | Per Capsule |
| N,N-dimethyl-3-[8-(methylthio)-dibenzo-[b,f]thiepin-10-yl]-2-propynylamine | 25.5 g. |
| Lactose | 159.5 g. |
| Maize Starch | 30.0 g. |
| Talc | 5.0 g. |
| | 220.0 g. |

The active ingredient, lactose and maize starch are mixed intimately with one another and passed through a comminuting machine. The mixture is now mixed thoroughly with the talc and filled into hard gelatin capsules.

EXAMPLE 15

Example 15

| A parenteral preparation of the following composition is prepared: Each 1 ml. ampule contains: | |
|---|---|
| N,N-dimethyl-3-[8-(methylthio)-dibenzo-[b,f]thiepin-10-yl]-2-propynylamine | 10.20 mg. (2% excess) |
| Methanesulfonic acid for injection | 2.22 mg. |
| Glucose for injection | 40.0 mg. |
| Water for injection q.s. ad | 1.0 ml. |

22.2 G. of methanesulfonic acid for injection, 102 g. of active ingredient and 400 g. of glucose are successively dissolved in a glass vessel in 8000 ml. of water for injection with stirring at room temperature.

Subsequently, water for injection is added to a total volume of 10,000 ml. The solution is either aseptically filtered, filled into colorless ampules, gassed with nitrogen and sealed, or filled into colorless ampules, gassed with nitrogen, sealed and subsequently sterilized in a current of steam or autoclaved at 120° C. for 30 minutes.

Instead of the active ingredients used in Examples 9-15, there can, of course, also be used in the preparations described therein, other dibenzo[b,f]-thiepin derivatives of the present invention, for example:

N,N-dimethyl-3-(8-chloro-3-methoxy-dibenzo[b,f]-thiepin-10-yl)-2-propynylamine or its methanesulfonate salt;

N,N-dimethyl-3-(8-chloro-dibenzo [b,f]thiepin-10-yl)-2-propynylamine or its maleate or methanesulfonate salt. Exemplary end products encompassed by claim 1 are also, for example, the following:

the compounds corresponding to the end products of Examples 1-8 and to the above compounds which are methyl substituted in 11-position;

the compounds corresponding to the foregoing which are N-methyl, N,N-diethyl, N,N-dihydroxyethyl amines or N'-methylpiperazines instead of N,N-dimethylamines; and the N-oxides of the aforegoing compounds.

We claim:

1. A compound of the formula

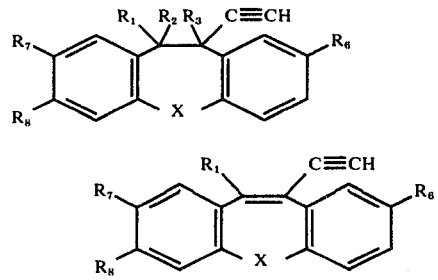

and wherein X is oxygen or sulfur; $R_1$ and $R_2$, independently, are hydrogen or lower alkyl; $R_3$ is hydrogen; $R_6$ is lower alkyl, lower alkyl-sulfonyl, hydroxy, lower alkoxy, lower alkylthio, di-(lower alkyl)-sulfamoyl, halogen, trifluoromethyl, nitro, amino or di-(lower alkyl)-amino; and $R_7$ and $R_8$, independently, are hydrogen, lower alkyl-sulfonyl, hydroxy, lower alkyl, lower alkoxy, lower alkylthio, di-(lower alkyl)-sulfamoyl, halogen, trifluoromethyl, nitro, amino or di-(lower alkyl)-amino.

2. A compound in accordance with claim 1, 10-ethynyl-8-trifluoromethyl-dibenzo[b,f]thiepin.

* * * * *

UNITED STATES PATENT AND TRADEMARK OFFICE
CERTIFICATE OF CORRECTION

PATENT NO. : 4,005,105
DATED : January 25, 1977
INVENTOR(S) : Jean-Pierre Kaplan & Emilio Kyburz It is certified that error appears in the above-identified patent and that said Letters Patent are hereby corrected as shown below:

Cover Sheet -    [56] References Cited
Foreign Patents or Applications

| | | |
|---|---|---|
| 7,588 | 1964 | Netherlands |
| 6,494 | 1964 | South Africa |
| 443,344 | 1964 | Switzerland | should be:

[56] References Cited
Foreign Patents or Applications

| | | |
|---|---|---|
| 6,407,588 | 1964 | Netherlands |
| 65/6494 | 1964 | South Africa |
| 443,344 | 1964 | Switzerland |

Signed and Sealed this sixteenth Day of August 1977

[SEAL]

Attest:

RUTH C. MASON
*Attesting Officer*

C. MARSHALL DANN
*Commissioner of Patents and Trademarks*